(12) United States Patent
Matt

(10) Patent No.: US 7,188,035 B2
(45) Date of Patent: Mar. 6, 2007

(54) CORIOLIS MASS FLOW METER FOR MEASURING A CONCENTRATION

(75) Inventor: Christian Matt, Aesch (CH)

(73) Assignee: Endress + Hauser Flowtec AG, Reinach (CH)

( * ) Notice: Subject to any disclaimer, the term of this patent is extended or adjusted under 35 U.S.C. 154(b) by 0 days.

(21) Appl. No.: 10/504,066

(22) PCT Filed: Feb. 26, 2003

(86) PCT No.: PCT/EP03/01957
§ 371 (c)(1),
(2), (4) Date: May 11, 2005

(87) PCT Pub. No.: WO03/076879
PCT Pub. Date: Sep. 18, 2003

(65) Prior Publication Data
US 2005/0228598 A1  Oct. 13, 2005

(30) Foreign Application Priority Data
Mar. 8, 2002 (DE) .................. 102 10 061

(51) Int. Cl.
G01F 1/00 (2006.01)
G01F 7/00 (2006.01)
G06F 19/00 (2006.01)

(52) U.S. Cl. .................... 702/45
(58) Field of Classification Search ............ 702/45
See application file for complete search history.

(56) References Cited

U.S. PATENT DOCUMENTS

| 4,773,257 A |   | 9/1988 | Aslesen et al. |
|---|---|---|---|
| 5,317,928 A | * | 6/1994 | Young .................... 73/32 R |
| 5,497,665 A | * | 3/1996 | Cage et al. ............ 73/861.356 |
| 5,734,112 A | * | 3/1998 | Bose et al. ............. 73/861.56 |
| 6,429,126 B1 | * | 8/2002 | Herner et al. ............ 438/680 |
| 6,513,393 B1 | * | 2/2003 | Eckert et al. .......... 73/861.357 |
| 6,557,422 B1 | * | 5/2003 | Kolahi .................. 73/861.357 |

FOREIGN PATENT DOCUMENTS

| DE | 696 07 756 T2 | 8/2000 |
|---|---|---|
| JP | 07294406 A | 11/1995 |
| WO | WO 01/67052 A1 | 9/2001 |

* cited by examiner

Primary Examiner—John Barlow
Assistant Examiner—Aditya S. Bhat
(74) Attorney, Agent, or Firm—Bacon & Thomas

(57) ABSTRACT

In a Coriolis mass flow meter for determining the concentration of a flowing fluid, a concentration function is stored in a concentration evaluating unit. This enables the user to produce a concentration value at given temperature and density of the medium appropriate for a given application.

1 Claim, 2 Drawing Sheets

US 7,188,035 B2

CORIOLIS MASS FLOW METER FOR MEASURING A CONCENTRATION

FIELD OF THE INVENTION

The invention relates to a Coriolis mass flow meter for measuring concentration.

BACKGROUND OF THE INVENTION

Coriolis mass flow meters are used in many cases for determining mass flow of a fluid in a section of a pipeline. In this, the fluid flows through at least one oscillating measuring tube. In most Coriolis mass flow meters, one oscillation exciter and two oscillation sensors are arranged on the measuring tube. Measuring tube and fluid form, together, an oscillatable system, which is normally excited to its resonance frequency. The resonance frequency depends on, among other things, the material and the dimensions of the measuring tube. It varies, additionally, with the density of the flowing fluid. In some cases, the measuring tube is not excited to the resonance frequency, but, instead, to a neighboring frequency. The two oscillation sensors register the oscillatory motion of the measuring tube at two locations spaced from one another in the direction of flow and convert the oscillatory movements of the measuring tube to sensor signals. Both sensor signals have the same frequency as the oscillatory movement of the measuring tube, but they are shifted in phase relative to one another. The phase shift between these two sensor signals is a measure of the mass flow rate.

The sensor signals are evaluated in a signal processing unit and converted into a signal proportional to the mass flow rate. Besides the mass flow rate, other properties of the fluid can also be determined, for example its density. For this purpose, the frequency of the oscillatory motion of the measuring tube is evaluated and, if need be, the temperature of the flowing fluid is determined.

Such a Coriolis mass flow meter is known from the commonly-owned German patent application DE 100 45 537.

Often in industrial processes, the concentration of a solution is a measured quantity of interest. This is true for mass- and volume-concentrations, as well as for various industry-specific concentration specifications, such as °Oechsle in wine-production or °Plato in beer brewing. A basic ingredient for the measurement of concentration in most cases is the density of the fluid. Correspondingly, various density functions, for example °Brix, °Plato, °Balling, °API, are already implemented in the Coriolis mass flow meters Promass 63 and Promass 83 of the firm Endress+Hauser®.

Various concentration measures are, however, not defined unequivocally in the literature. Different users apply different definitions, which then lead to different concentration values.

In the case of conventional Coriolis mass flow meters, the output of different concentration values is only conditionally possible.

It is an object of the invention to provide a Coriolis mass flow meter for concentration measurement, which is simple and economical to manufacture.

This object is achieved by a Coriolis mass flow meter for concentration measurement including a digital signal processor, which determines from the senior signals and the temperature signals of a transducer the density of the flowing fluid, and a concentration evaluating unit connected thereafter, in which a concentration curve is stored.

Advantageous further developments of the invention are given in the dependent claims.

An essential idea of the invention is the providing in the Coriolis mass flow meter for measuring concentration a unit, in which a predeterminable concentration curve is stored.

There follows a more detailed explanation of the invention on the basis of an example of an embodiment, as illustrated in the drawings, which show as follows:

DETAILED DESCRIPTION OF THE PREFERRED EMBODIMENT

Figure 1:
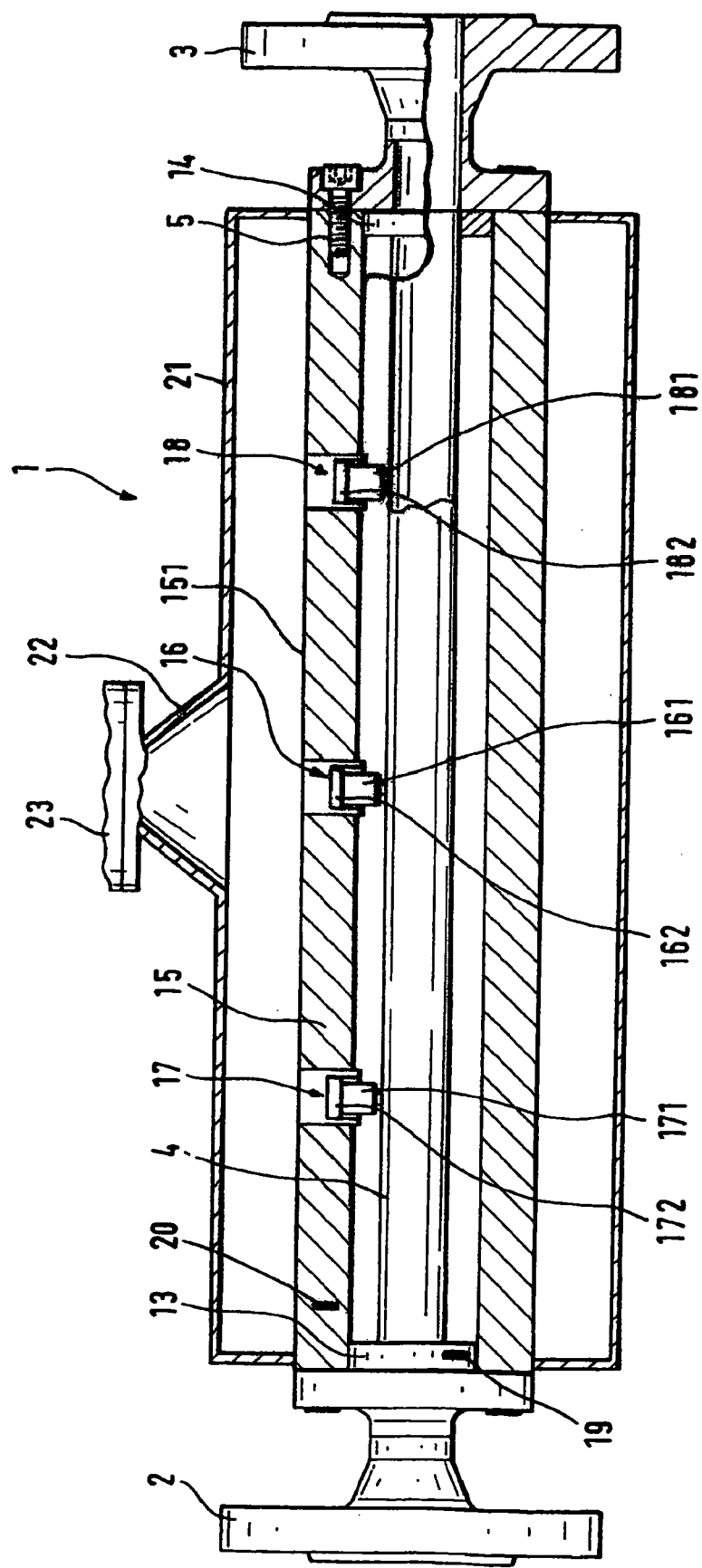
FIG. 1 a schematic drawing of the transducer of a Coriolis mass flow meter.

FIG. 1 is a schematic drawing of a transducer 1 for a Coriolis mass flow meter. The transducer 1 is arranged in a pipeline, which is not shown in further detail. A fluid F flows in the pipeline. The mass flow rate of the fluid is one of the parameters of interest. The connection with the pipeline is by way of the two flanges 2, 3.

The transducer 1 includes a single, straight measuring tube 4, which is secured at its inlet end at the flange 2 by an end-plate 13 and at its outlet end at flange 3 by an end-plate 14.

The flanges 2, 3 and the end-plates are secured on or in a support tube 15.

For causing the measuring tube to oscillate, an oscillation exciter 16 is arranged at the middle of the measuring tube 4 between the two end-plates 13, 14. The oscillation exciter 16 can be, for example, an electromagnetic drive composed of a permanent magnet 161 and a coil 162. The coil 162 is secured to the tube 15 and the permanent magnet to the measuring tube 4. The amplitude and the frequency of the bending oscillation of the measuring tube 4, which occurs in the plane of the drawing, are controlled by the electrical current flowing in the coil 162.

Coriolis forces arise in the plane of the drawing, when a fluid F flows through the measuring tube 4. A result of these forces is that all points of the measuring tube 4 no longer oscillate in phase.

The oscillatory motion of the measuring tube 4 is registered with the help of two oscillation sensors 17, 18, which are arranged likewise on the support tube, about symmetrically on either side of the oscillation exciter 16. The oscillation sensors 17, 18 can be, for example, electromagnetic converters, which are constructed similarly to the oscillation exciter 16.

The two permanent magnets 171, 181 thereof are secured to the measuring tube 4 and the two coils 172, 182 are secured to the support tube 15. The motion of the measuring tube 4 causes the magnets 171, 181 to induce voltages in the associated coils 172, 182, and these voltages are tapped as analog sensor signals X17 respectively X18.

Two temperature sensors 20, 19 serve for registering the temperature of the fluid.

Temperature sensor 19 is located on end-plate 13 and temperature sensor 20 is on support tube 15.

Transducer 1 is connected to a digital signal processing unit DSP. The signal processing unit DSP delivers at its outputs the measurements mass flow rate, density and temperature of the flowing fluid F.

Figure 2:
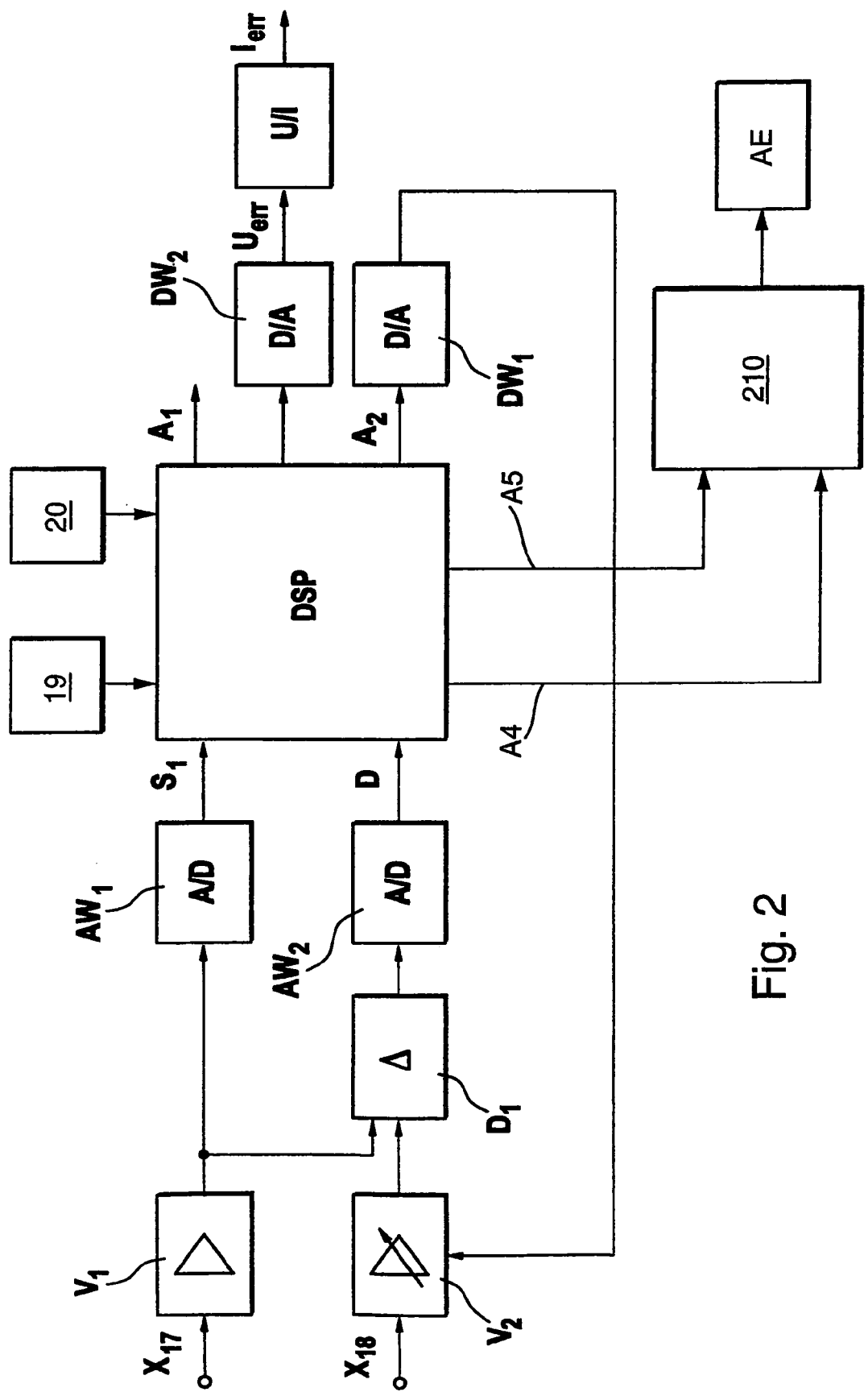
FIG. 2 a block diagram of a signal processing unit for a Coriolis mass flow meter having a concentration determining unit.

FIG. 2 is a block diagram of the signal processing unit associated with the transducer 1. Among other things, it evaluates the sensor signals $X_{17}$, $X_{18}$ and it regulates the oscillation excitations of the measuring tube 4. The two sensor signals $X_{17}$ and $X_{18}$ are fed, respectively, to a first amplifier $V_1$ and a second amplifier $V_2$. The amplification of the amplifier $V_2$ is variable via an adjustable amplification factor.

The amplifier $V_1$ is connected to an A/D converter $AW_1$ and to a difference stage $D_1$ in parallel therewith. The amplifier $V_2$ is connected to a second input of the difference stage $D_1$. The output of the difference stage $D_1$ is connected to a second A/D converter $AW_2$. The two outputs of the A/D converters $AW_1$ and $AW_2$ provide, respectively, the sensor signal $S_1$ and the difference signal D, both in digital form. Both outputs are connected to respective inputs of the digital signal processing unit DSP.

The two temperature sensors 19 and 20 are likewise connected to respective inputs of the signal processing unit DSP.

The signal processing unit delivers, in known manner, on plural outputs $A_1$, A4, A5 the values of the mass flow rate, the density and the temperature, respectively, of the fluid F. Additionally, the signal processing unit DSP controls the exciter current, which drives the oscillation excitation of the measuring tube 4 and the amplification factor VF of the amplifier $V_2$.

The signal processing unit is additionally connected to a concentration determining unit 210. In the concentration determining unit 210, density and temperature of the fluid are evaluated. The concentration determining unit 210 is connected to a display unit AE for displaying the desired concentration value. Besides presenting the concentration value in the display unit AE, a transmitting of the concentration value to a superordinated evaluating unit (not shown in further detail) is also possible.

The concentration determining unit 210 stores a concentration curve C as a function of density and temperature of the fluid. Input of the current density value and the current temperature of the fluid enables easy determination of the desired concentration.

One possibility for storing the concentration curve is to store the corresponding polynomial coefficients. The polynomial coefficients can be easily determined by providing concentration values for particular density and temperature values and conducting a corresponding polynomial approximation.

In the simplest case, this involves a two-dimensional polynomial.

$$c(\rho, \vartheta) = \sum_{i=0}^{M} a\rho^i + \sum_{i=1}^{Z} b\vartheta^i$$

The polynomial degree of the density polynomial is preferably M=4, the polynomial degree of the temperature polynomial Z=3.

By entering various concentration values, a user can produce a concentration specification tuned to one's application.

The invention claimed is:

1. A coriolis mass flow meter for determining the concentration of a flowing fluid comprising:
    a digital signal processor (DSP), which determines from sensor signals and temperature signals of a transducer the density of a flowing fluid; and
    a concentration evaluating unit connected thereafter, in which a concentration curve is stored as a two dimensional polynomial, $$c(\rho, \vartheta) = \sum_{i=0}^{4} a\rho^i + \sum_{i=1}^{3} b\vartheta^i,$$

wherein:
    the degree of the density polynomial $\rho^i$ is 4 and the degree of the temperature polynomial $\vartheta^i$ is 3.

* * * * *